United States Patent [19]

Nakano et al.

[11] Patent Number: 5,366,966
[45] Date of Patent: Nov. 22, 1994

[54] COMPOUND UCE6

[75] Inventors: Hirofumi Nakano; Noboru Fujii; Yoshinori Yamashita; Youichi Uosaki; Shigeru Chiba, all of Tokyo; Shigeo Katsumata; Yukari Tsuji, both of Shizuoka, all of Japan

[73] Assignee: Kyowa Hakko Kogyo Co., Ltd., Tokyo, Japan

[21] Appl. No.: 70,962

[22] Filed: Jun. 4, 1993

[30] Foreign Application Priority Data

Jun. 10, 1992 [JP] Japan .................... 4-150854

[51] Int. Cl.$^5$ .................. C07C 15/38; C12P 15/00
[52] U.S. Cl. ..................... 514/152; 552/201
[58] Field of Search .................. 552/201; 514/152

[56] References Cited
FOREIGN PATENT DOCUMENTS 1917874 11/1969 Germany ................. 552/201

OTHER PUBLICATIONS

CRC Handbook of Antibiotic Compounds, vol. 3; Berdy, Janos, 1980.

*Primary Examiner*—Johann Richter
*Assistant Examiner*—Rebecca Cook
*Attorney, Agent, or Firm*—Nixon & Vanderhye

[57] ABSTRACT

A compound represented by formula (I):

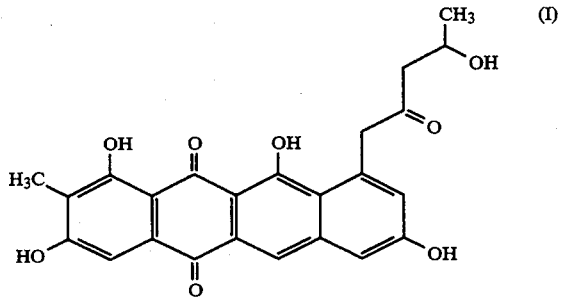

or a pharmaceutically acceptable salt thereof is provided, which has an excellent antitumor activity.

2 Claims, No Drawings

COMPOUND UCE6

FIELD OF THE INVENTION

This invention relates to a novel compound UCE6 which has an antitumor activity and is useful as an antitumor agent.

BACKGROUND OF THE INVENTION

It is reported in the literature that several antibiotics, such as anthracycline, have an anthraquinone skeleton [CRC Handbook of Antibiotic Compounds, CRC Press, U.S.A. (1981)].

SUMMARY OF THE INVENTION

An object of the present invention is to provide a compound having an excellent antitumor activity.

The present inventors found that a substance having an antitumor activity is produced in a culture obtained by incubating a microorganism (hereinafter referred to as strain UOE6) separated from soil in a medium. The active substance was isolated and purified from the medium. The investigation of the physicochemial properties of the purified active substance revealed that the purified active substance is a novel compound. The novel compound is named UCE6.

According to the present invention, a novel compound UCE6 which is represented by the following formula (I):

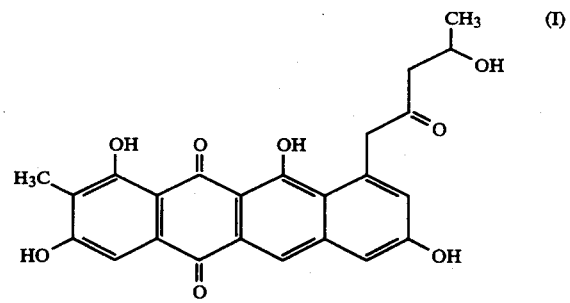

or a pharmaceutically acceptable salts thereof.

UCE6 provides antitumor activity.

This compound can be obtained by cultivating a microorganism belonging to actinomycetes.

DETAILED DESCRIPTION OF THE INVENTION

The present invention is described below in greater detail.

Physicochemical Properties of UCE6:

(1) Molecular weight: 436.

(2) Molecular formula: $C_{24}H_{20}O_8$.

(3) Mass spectrometry: secondary ion mass spectrum (matrix: m-nitrobenzyl alcohol): m/z; 437 (M+H)+, 375, 350, 329, 280, 278, 238, 222, 207. High-resolution fast atom bombardment (FAB) mass spectrum (matrix: m-nitrobenzyl alcohol): m/z found: 437.1242 (M+H)+ calculated: 437.1236 (for $C_{24}H_{21}O_8$).

(4) Specific rotation: $[\alpha]_D^{22} = +350°$ (c=0.0021, methanol).

(5) Ultraviolet absorption spectrum: (measured in methanol) $\lambda_{max}$ nm ($\epsilon$); 477 (15,000), 334 (14,800), 307 (27,600), 294 (25,300), 283 (26,100), 240 (25,300), 217 (23,500).

(6) Infrared absorption spectrum (KBr method): $\nu_{max}$ cm$^{-1}$; 361, 1695, 1655, 1603, 1441, 1377, 1323, 1277, 1217.

(7) $^{13}$C-NMR spectrum (100 MHz, DMSO-$d_6$ solution): δ ppm; 184.5, 182.6, 167.0, 162.2, 158.7, 139.0, 137.7, 132.3, 129.5, 128.9, 128.2, 123.7, 121.3, 118.9, 116.9, 111.8, 108.9, 107.7, 62.7, 51.4, 50.0, 23.8, 8.3 (having an unobserved signal).

(8) $^1$H-NMR spectrum (500 MHz, DMSO-$d_6$ solution): δ ppm; ca. 13.5 (1H, br. s), 7.75 (1H, m), 7.14 (1H, m), 7.00 (1H, m), 6.82 (1H, m), 4.22 (2H, m), 4.17 (1H, m), 2.68 (1H, dd, J=15.7, 7.3 Hz), 2.57 (1H, dd, J=15.7, 5.0 Hz), 1.99 (3H, d, J=1.8 Hz), 1.13 (3H, d, J=6.2 Hz).

(9) Solubility: soluble in dimethylsulfoxide (DMSO), N,N-dimethylformamide and pyridine and hardly soluble in water, ethanol, methanol, ethyl acetate and chloroform.

(10) Color reaction: positive in anisaldehyde and iodine.

(11) Appearance: a red powder.

(12) Thin layer chromatography: Rf 0.61 [developed with n-hexane: ethyl acetate: methanol (5:5:1, v/v) on a silica gel thin layer (HPTLC plate Art. 5715, mfd. by Merck). Rf 0.49 [developed with chloroform:methanol=10:1]. After the completion of the development, a spot of UCE6 can be detected by UV absorption.

The pharmaceutically acceptable salts of UCE6 include pharmaceutically acceptable metal salts. As the metal salt, there are alkali metal salts such as sodium salt and potassium sats, alkaline earth metal salts such as magnesium salt and calcium salt.

Biological activities of UCE6 is described below.

(A) Inhibition on the Growth of HeLaS3 Cells 0.1 ml portions of a $3 \times 10^4$ cell/ml suspension of HeLaS3 cells [American Type Culture Collection (ATCC) CCL2.2]. in Minimum Essential Medium (MEM) medium (mfd. by Nissui Seiyaku) containing 10% of calf fetal serum and 2 mM of glutamine (hereinafter referred to as the medium A) were pipetted into a 96-well microtiter plate. 0.05 ml of the test compound optionally diluted with the medium A is added to each well, followed by incubating in a carbon dioxide gas incubator at 37° C. for 72 hours. After removing supernatant the culture 0.1 ml of the medium A containing 0.02% of Neutral Red is added to the residue. The cells are cultivated in the carbon dioxide gas incubator at 37° C. for additional one hour to thereby stain the cells. After removing the supernatant of culture, the residue was washed with saline once. The pigment is extracted with 0.001 N hydrochloric acid/30% ethanol and the absorbance at 550 nm is measured with a microplate reader. Then IC$_{50}$ (the concentration of the test compound capable of inhibiting the growth of the cells at a ratio of 50%) is calculated on the basis of the comparison between the absorbance of untreated cells and that of the test compound-treated cells (at various concentration of the test compound). Results are shown in Table 1.

TABLE 1

| Compound | IC$_{50}$ ($\mu$M) |
|---|---|
| UCE6 | 0.018 |

A method for producing UCE6 is described below.

UCE6 can be obtained by cultivating a microorganism (belonging to actinomycetes and being capable of producing UCE6) in medium, accumulating UCE6 in a culture and recovering UCE6 from the culture.

As a UCE6-producing microorganism, any strain may be used so long as it belongs to actinomycetes and capable of producing UCE6. Furthermore, mutants of such a strain obtained by artificial mutation techniques (for example, UV irradiation, X-ray irradiation, treatment with mutagenic agent) or spontaneous mutation are also usable in the present invention. As a typical example of the strain, strain UOE6 may be cited.

The mycological characteristics of the actinomycetes strain UOE6 are as follows.

1. Morphology

In a usual agar medium, the strain UOE6 forms branched substrate hyphae having septal walls. Neither the formation of aerial hyphae nor characteristic segmentation in the substrate hyphae is observed. Neither any spore, sporangium nor sclerotium is formed.

2. Growth in Various Media

The strain UOE6 moderately or vigorously grows in synthetic and natural media which are commonly employed and shows orange or brown substrate hyphae. In some media, it produces a brown soluble pigment.

The characteristics of the growth and the color observed when the strain UOE6 is cultivated in various media at 28° C. for 20 days are given hereinbelow. Colors are expressed in accordance with the classification described in Color Harmony Manual [Container Corporation of America].

1. Glucose/aspargine Agar Medium
   Growth and color of substrate hyphae: somewhat good, light tan (3 gc).
   Soluble pigment: formed, pale brown.
2. Glycerol/aspargine Agar Medium
   Growth and color of substrate hyphae: somewhat poor, light apricot (4 ea).
   Soluble pigment: none.
3. Sucrose/nitrate Agar Medium
   Growth and color of substrate hyphae: moderate, light apricot (4 ea).
   Soluble pigment: slightly formed, pale brown.
4. Starch/inorganic Salt Agar Medium
   Growth and color of substrate hyphae: moderate, pastel orange (4 ic).
   Soluble pigment: formed, pale brown.
5. Tyrosine Agar Medium
   Growth and color of substrate hyphae: moderate, dusty orange (4 lc).
   Soluble pigment: none.
6. Enriched Agar Medium
   Growth and color of substrate hyphae: poor, light tan (3 gc).
   Soluble pigment: slightly formed, pale brown.
7. Malt Extract/yeast Extract Agar Medium
   Growth and color of substrate hyphae: good, pastel orange (4 ic).
   Soluble pigment: slightly formed, pale brown.
8. Oatmeal Agar Medium
   Growth and color of backside: somewhat good, light orange (4 ia).
   Soluble pigment: slightly formed, pale brown.

3. Physiological Properties

Physiological properties of the strain UOE6 are described below. The growth temperature range is determined after incubating the strain for 7 days, while other data are obtained after incubating it for 1 to 3 weeks.

(1) Utilization of carbon source: on agar medium, L-arabinose, D-xylose, D-glucose, D-fructose, sucrose, L-rhamnose, raffinose and D-mannitol are utilized for the UOE6. But inositol is not utilized for the UOE6.

(2) Action on milk: it causes neither coagulation nor liquefaction.

(3) Hydrolysis of starch: yes.

(4) Growth temperature range: 15 to 35° C.

(5) Production of melanoid pigment: not observed on definite media (tyrosine agar medium, peptone/yeast-/iron agar medium).

(6) Liquefaction of gelatin: not grown on a definite medium (glucose/peptone gelatin medium).

4. Formation of Cell Wall

Amino acids including alanine, glutamic acid, 3-hydroxy-diaminopimelic acid and glycine and saccharides including xylose and arabinose are detected from the cell wall of the strain UOE6 prepared by the method of Kawamoto et al. [J. Bacteriol., 146, 57–534 (1981)] (cell wall type II, saccharide pattern D).

Based on these characteristics of the UOE6, the strain UOE6 is classified into actinomycetes. Since no spore is adhered to UOE6, it is difficult to determine the genus of the strain.

Under the Budapest treaty, this strain has been deposited with Fermentation Research Institute of the Agency of Industrial Science and Technology of 1–3, Higashi 1-chome, Tsukuba-shi, Ibaraki 305 Japan as the accession number FERM BP-3877 since May 28, 1992.

A method for incubating the UCE6-producing strain is described below.

In order to cultivate the UCE6-producing strain in the present invention, a usual cultivation method of actinomycetes can be used. As a medium of cultivation, either a synthetic medium or a natural medium may be used so long as it contains an utilizable carbon source, a nitrogen source, inorganic matters and required promoting substances of the growth of the strain and/or of the production of UCE6.

As the carbon source, for example, glucose, starch, dextrin, mannose, fructose, sucrose, lactose, xylose, arabinose, mannitol and molasses may be used either singly or combinedly. Furthermore, hydrocarbons, alcohols and organic acids are also usable, so long as it is utilized for the strain.

As the nitrogen source, for example, ammonium chloride, ammonium nitrate, ammonium sulfate, sodium nitrate, urea, peptone, meat extract, yeast extract, dry yeast, corn steep liquor, soybean flour and casamino acids may be used either singly or combinedly. In addition, the medium may contain inorganic salt(s) such as sodium chloride, potassium chloride, magnesium sulfate, calcium carbonate, potassium dihydrogen phosphate, ferrous sulfate, calcium chloride, manganese sulfate, zinc sulfate or copper sulfate, if required. Furthermore, it may contain appropriate trace component(s) capable of promoting the growth of the strain and/or the production of UCE6.

As the cultivation method, liquid culture or submerged agitation culture may be suitably selected. The incubation is carried out at a temperature of 16° to 37° C., preferably 25° to 32° C., and at a pH 4 to 10, preferably 6 to 8. Usually, the cultivation is completed within 1 to 7 days and thus the target product UCE6 is formed and accumulated in the culture broth and cells. The pH value of the culture medium is controlled with the use of aqueous ammonia or an ammonium carbonate solution. When the content of the product in the culture medium reaches the maximum level, the incubation is ceased.

The product UCE 6 is isolated and purified from the culture by a method commonly used for isolating and purifying a microbial metabolite from its culture. For example, the culture is divided into the culture supernatant and cells by filtering and the cells are extracted with, for example, chloroform or acetone. Then the extract is combined with the culture supernatant and passed through a column packed with a polystyrene adsorbent such as Diaion HP20 (mfd. by Mitsubishi Kasei Corporation) for adsorption of the active component. The active component is eluted with, for example, ethyl acetate or acetone. The eluate is concentrated and UCE6 is obtained therefrom by, for example, silica gel column chromatography or high performance liquid chromatography. During the incubation and purification procedures, the behaviors of UCE6 can be monitored by using the UV absorption of UCE6 as an indicator.

The UCE6 can be prepared by basically the known synthetic method as described in Cameron, D. W. et al, Tetrahedron Letters, 3, 5593–5596 (1992).

In case that salts of UCE6 are desired to be obtained, when the crude UCE6 is obtained in the form of a salt, UCE6 may be purified as it is. Further in case that UCE6 is obtained in a free form, salts may be formed in a conventional manner.

The UCE6 is useful as an anti-tumor agent, which can be used directly as such, or in various dosage forms. For example, where UCE6 is used in the form of an injeciton, it may be dissolved in a diluent conventinally used in the art, such as a physiological saline, or glucose, lactose or mannitol solution for injection. Alternatively, UCE6 may be freeze-dried according to a conventional manner to give a product for injection or may be prepared into injectable powder by adding sodium chloride thereto. In addition, the injection may also contain an auxiliary agent such as polyethylene glycol, HCO-60 (surfactant manufactured by Nikko Chemical Co., Ltd.), as well as a carrier such as ethanol and/or liposome or cyclodextrin. These injection are generally used for intraveous administration but may also be used for intra-arterial, intra-peritoneal or intra-thoracial administration.

UCE6 may also be administered orally by mixing with an appropriate excipient, a disintegrator, a binder, a lubricant, etc. in a conventional manner to prepare a tablet, a granule, a powder or a syrup. Furthermore, UCE6 may be mixed with a conventionally used carrier and formed into a suppository for rectum administration.

Dosage may appropriately vary depending upon the administration route, the age of a patient and the condition of a patient. The administration route, may also be varied according to the condition of a patient and the dosage. For example, UCE6 can be intermittently administered in a dose of 10 to 60 mg/kg once a day.

The following Example is provided to further illustrate the present invention, but it is not to be construed to limit the scope of the present invention.

EXAMPLE 1

Actinomycetes strain UOE6 (FERM BP-3877) was used as a seed strain. This strain was inoculated into 300 ml of a seed medium (pH 7.2 before sterilization) comprising 5 g/l of Bacto Trypton (mfd. by Difco), 5 g/l of yeast extract, 3 g/l of meat extract, 10 g/l of soluble starch, 10 g/l of glucose and 5 g/l of calcium carbonate contained in a 2 l Erlenmeyer flask and then incubated at 28° C. for 120 hours under shaking at 200 rpm.

The seed culture medium thus obtained was transferred at a ratio of 5% by volume into 18 l of a fermentation medium of the following composition contained in a 30 l jar fermentor. The seed culture was cultivated therein at 28° C. under aerating at a rate of 18 l/min and agitating at 200 rpm.

Composition of fermentation medium: 50 g/l of soluble starch, 15 g/l of soybean flour, 0.5 g/l of $KH_2PO_4$, 0.5 g/l of $MgSO_4.7H_2O$, 0.5 g/l of $Mg_3(PO_4)_2.8H_2O$ (pH 7.0 before sterilization, adjusted with NaOH).

The cultivation was continued for 144 hours without controlling the pH of the medium.

36 l of methanol was added to the culture to thereby extract UCE6. To the methanol extract was added 18 l of water and the mixture was passed through a column packed with a nonionic porous resin Diaion HP20 (mfd. by Mitsubishi Kasei Corporation). Then, active substance (including UCE6) was adsorbed with the resin. After eluting the impurities with a mixture of methanol and water (85:15, v/v), the active substance was eluted with methanol. The methanol fraction was concentrated and poured onto a silica gel column (Lichroprep-Si60, Art 9390, mfd. by Merck), followed by developing with hexane/ethyl acetate/methanol (8:5:1, v/v). The active fraction thus eluted was concentrated and poured onto a Sephadex LH20 column (mfd. by Pharmacia), followed by eluting with methanol. The active fraction thus eluted was concentrated and dried. Thus 38 mg of UCE6 was obtained as a red purple powder.

According to the present invention, a novel fermentation product UCE6 having an antitumor activity is provided.

While the invention has been described in detail and with reference to specific examples thereof, it will be apparent to one skilled in the art that various changes and modifications can be made therein without departing from the spirit and scope thereof.

What is claimed is:

1. A compound represented by formula (I):

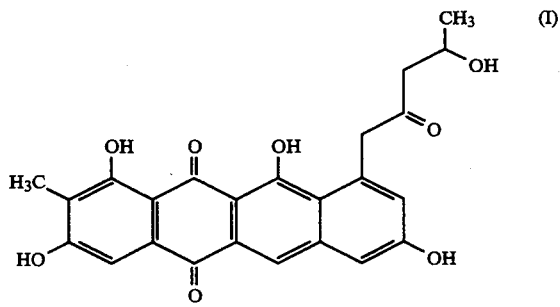

or a pharmaceutically acceptable salt thereof.

2. A composition comprising the compound of claim 1 or a pharmaceutically acceptable salt thereof and a pharmaceutically acceptable carrier.

* * * * *